United States Patent
Peglion et al.

(10) Patent No.: US 6,452,015 B2
(45) Date of Patent: Sep. 17, 2002

(54) CYCLOBUTAINDOLECARBOXAMIDE COMPOUNDS

(75) Inventors: Jean-Louis Peglion, Le Vesinet; Bertrand Goument, Viroflay; Mark Millan, Le Pecq; Françoise Lejeune, Saint Cloud; Didier Cussac, Chatou, all of (FR)

(73) Assignee: Les Laboratoires Servier, Courbevoie (FR)

(*) Notice: Subject to any disclaimer, the term of this patent is extended or adjusted under 35 U.S.C. 154(b) by 0 days.

(21) Appl. No.: 09/833,826

(22) Filed: Apr. 12, 2001

(30) Foreign Application Priority Data

Apr. 13, 2000 (FR) .............................. 00.04743

(51) Int. Cl.[7] ...................... C07D 401/00; C07D 401/02
(52) U.S. Cl. .................................... 546/276.7
(58) Field of Search ........................... 546/278.1, 276.7

(56) References Cited

FOREIGN PATENT DOCUMENTS

WO    WO 99/43319    *    2/1999

OTHER PUBLICATIONS

Psychopharmacology 2000, 152, 55–56.
Neuropharmacology 1997, 36 (4/5), 609–620.
British Journal of Pharmacology 1996, 117, 427–434.
Neuropharmacology 2001, 41, 186–199.
Japanese Journal of Pharmacology, 76, 297–304.
Psycopharmacology 1993, 110, 53–59.
Pharmacology Biochemistry & Behavior, 39, 729–736.
Journal of Psychopharmacology 2000, 14 (2), 114–138.
Journal of Psychopharmacology 1997, 11(2), 123–131.
Schizophrenia Bulletin, 2001, 27 (3), 431–442.
Arch. Gen. Psychiatry, 1996, 53, 448–455.
Psychopharmacology 1994, 115, 285–288.
Behavioural Brain Research 2000, 114, 135–143.
Neuropsychopharmacology 1999, 21(5), 601–610.
Neuropsychopharmacology 1997, 17(2), 92–99.

* cited by examiner

Primary Examiner—Alan L. Rotman
Assistant Examiner—Binta Robinson
(74) Attorney, Agent, or Firm—The Firm of Hueschen and Sage; G. Patrick Sage

(57) ABSTRACT

A compound selected from those of formula (I):

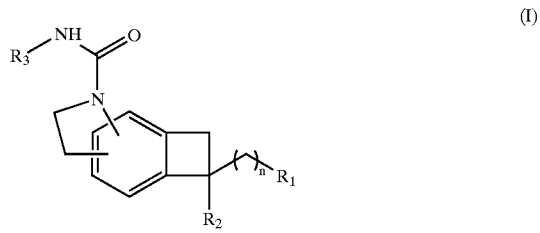

wherein:
  n represents integer from 0 to 6,
  $R_1$ represents a group selected from hydrogen, hydroxy, cyano, alkoxy, alkoxycarbonyl, carboxy, optionally substituted aminocarbonyl, and $NR_4R_5$ wherein $R_4$, and $R_5$ are as defined in the description,
  $R_2$ represents a group selected from hydrogen, alkyl, hydroxymethyl,

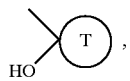

and -U-V-W wherein T, U, V, and W are as defined in the description,
  and
  $R_3$ represents a group selected from hydrogen, linear or branched $(C_1-C_6)$alkyl, aryl, and, heteroaryl,
its isomers, and also addition salts thereof with a pharmaceutically-acceptable acid or base, and medicinal products containing the same are useful in the treatment of CNS disorders.

7 Claims, No Drawings

CYCLOBUTAINDOLECARBOXAMIDE COMPOUNDS

FIELD OF THE INVENTION

The present invention relates to new cyclobutaindolecarboxamide compounds, and pharmaceutical compositions containing them.

The compounds of the present invention are useful in the treatment of disorders of the central nervous system, such as anxiety, panic attacks, obsessive-compulsive disorders, phobias, impulsive disorders, drug abuse, cognitive disorders, psychoses, depression and mood disorders.

PRIOR ART DESCRIPTION

Numerous polycyclic and heterocyclic compounds containing a urea function have been described in the literature as antagonists of various serotonergic receptors, thus enabling them to be used in the treatment of disorders of the central nervous system. This applies more especially to the Patent Applications WO 95/29177, WO 96/23783 and WO 98/47868, while patent specification U.S. Pat. No. 5,514,690 describes aminocarbonylquinoline and indoline compounds and claims them for their property of activating potassium pumps. In addition to being new, the compounds of the present invention have proved very active in the treatment of disorders of the central nervous system, and more especially have demonstrated strong activity in the Vogel conflict test in the rat, and in the marble-burying test in the mouse. The results obtained in the first test allows the use of the compounds of the invention in the treatment of clinical phenomena associated with anxiety to be proposed, and the results obtained in the second test demonstrates the strong therapeutic potential of the compounds of the invention in the treatment of illnesses associated with mood disorders.

DETAILED DESCRIPTION OF THE INVENTION

The invention relates more especially to the compounds of formula (I):

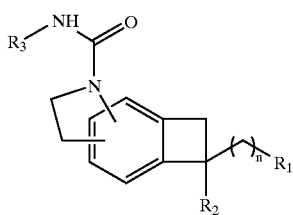

wherein:
n represents an integer of from 0 to 6,
$R_1$ represents a group selected from hydrogen, hydroxy, cyano, linear or branched ($C_1$–$C_6$)alkoxy, linear or branched ($C_1$–$C_6$)alkoxycarbonyl, carboxy, aminocarbonyl (the amino moiety optionally being substituted by one or two identical or different groups selected from linear or branched ($C_1$–$C_6$)alkyl, aryl and aryl-($C_1$–$C_6$)alkyl in which the alkyl moiety may be linear or branched) and $NR_4R_5$ wherein $R_4$ and $R_5$, which may be identical or different, represent a group selected from linear or branched ($C_1$–$C_6$)alkyl, aryl, aryl-($C_1$–$C_6$)alkyl in which the alkyl moiety may be linear or branched, heteroaryl, heteroaryl. ($C_1$–$C_6$)alkyl in which the alkyl moiety may be linear or branched, cycloalkyl, cycloalkyl-($C_1$–$C_6$)alkyl in which the alkyl moiety may be linear or branched, linear or branched ($C_2$–$C_6$)alkenyl and linear or branched ($C_2$–$C_6$)alkynyl,
$R_2$ represents a group selected from hydrogen, linear or branched ($C_1$–$C_6$)alkyl, hydroxymethyl, a group of formula

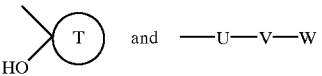

wherein:
T represents a monocyclic or polycyclic ($C_3$–$C_{12}$) cycloalkyl group, it being possible for one of the carbon atoms of the cycloalkyl optionally to be replaced by a group selected from oxygen, selenium, a group of formula $S(O)_p$ wherein p represents an integer of from 0 to 2 inclusive, and a group of formula $SiR_6R_7$ wherein $R_6$ and $R_7$, which may be identical or different, represent a linear or branched ($C_1$–$C_6$)alkyl group,
U represents a bond or a methylene group,
V represents a bond, an oxygen atom or a group $S(O)_q$ wherein q is an integer of from 0 to 2 inclusive, and
W represents a group selected from aryl, aryl-($C_1$–$C_6$) alkyl in which the alkyl moiety may be linear or branched, cycloalkyl, and cycloalkyl-($C_1$–$C_6$)alkyl in which the alkyl moiety may be linear or branched,
and
$R_3$ represents a group selected from hydrogen, linear or branched ($C_1$–$C_6$)alkyl, aryl and heteroaryl,
to their isomers, and also to addition salts thereof with a pharmaceutically acceptable acid or base.

An aryl group is to be understood as a group selected from phenyl, biphenyl, naphthyl, dihydronaphthyl, tetrahydronaphthyl, indanyl, indenyl and benzocyclobutyl, each of which groups is optionally substituted by one or more identical or different groups selected from halogen atoms, linear or branched ($C_1$–$C_6$)alkyl, hydroxy, linear or branched ($C_1$–$C_6$)-alkoxy, nitro, cyano, linear or branched ($C_1$–$C_6$)trihaloalkyl, amino, monoalkylamino, di-($C_1$–$C_6$) alkylamino in which the alkyl moieties may be linear or branched, ($C_1$–$C_6$)-trihaloalkoxy in which the alkoxy moiety may be linear or branched, amino($C_1$–$C_6$) alkylaminocarbonyl (the nitrogen atoms of each of the amino moieties optionally being substituted by identical or different linear or branched ($C_1$–$C_6$)alkyl groups), pyridyl, pyridyloxy and pyridyloxymethyl, the latter three groups optionally being substituted by a linear or branched ($C_1$–$C_6$) alkyl group.

A heteroaryl group is to be understood as an aromatic monocyclic system, or a bicyclic system in which one of the rings is aromatic and the other ring is aromatic or partially hydrogenated, having from 5 to 12 ring members and containing one, two or three identical or different hetero atoms selected from oxygen, nitrogen and sulphur, each of the groups optionally being substituted by one or more identical or different groups selected from the substituents described for the aryl group defined above.

A cycloalkyl group is to be understood as a mono- or poly-cyclic system having from 3 to 12 ring members and optionally containing one or more unsaturations, wherein the unsaturations do not confer an aromatic character to the said ring system.

Isomers is to be understood as optical isomers (enantiomers (enantiomers and diastereoisomers).

Amongst the pharmaceuticaly acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, oxalic, methanesulphonic, camphoric acid, etc.

Amongst the pharmaceutically acceptable bases there may be mentioned, without implying any limitation, sodium hydroxide, potassium hydroxide, triethylamine, tert-butylamine etc.

According to an advantageous embodiment of the invention, preferred compounds of the invention are compounds of formula (I) wherein $R_2$ represents a hydrogen atom.

According to another advantageous embodiment of the invention, preferred compounds of the invention are compounds of formula (I) wherein $R_2$ represents a group of formula

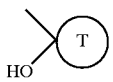

wherein T is as defined for formula(I), n is 1, and $R_1$ represents a cyano group or an amino group optionally substituted by one or two identical or different groups selected from linear or branched $(C_1–C_6)$alkyl and aryl-$(C_1–C_6)$alkyl in which the alkyl moiety may be linear or branched.

In another advantageous embodiment, preferred compounds of the invention are compounds of formula (I) wherein n is 0, $R_1$ represents a hydrogen atom or a cyano group and $R_2$ represents a group of formula -U-V-W wherein U represents a single bond, V represents a group of formula $S(O)_p$ wherein p is as defined for formula (I) and W represents an aryl group.

Especially advantageously, preferred compounds of the invention are compounds of formula (I) wherein n is 0, $R_1$ represents a hydrogen atom or a cyano group and $R_2$ represents a hydrogen atom.

The substituent $R_3$ preferred in accordance with the invention is the heteroaryl group and, more especially, the pyridyl group.

The following are preferred compounds of the invention:

N-(3-pyridyl)-2,3,5,6-tetrahydro-1H-cyclobuta[f]indole-1-carboxamide, 5-cyano-N-(3-pyridyl)-2,3,5,6-tetrahydro-1H-cyclobuta[f]indole-1-carboxamide, 6-cyano-N-(3-pyridyl)-2,3,5,6-tetrahydro-1H-cyclobuta[f]indole-1-carboxamide, 6-(hydroxymethyl)-N-(3-pyridyl)-2,3,5,6-tetrahydro-1H-cyclobuta[f]indole-1-carboxamide, 5-(hydroxymethyl)-N-(3-pyridyl)-2,3,5,6-tetrahydro-1H-cyclobuta[f]indole-1-carboxamide, 7-cyano-N-(3-pyridyl)-1,2,6,7-tetrahydro-3H-cyclobuta[e]indole-3-carboxamide, 7-(hydroxymethyl)-N-(3-pyridyl)-2,3,6,7-tetrahydro-1H-cyclobuta[g]indole-1-carboxamide, 6-[(dimethylamino)methyl]-6-(1-hydroxycyclohexyl)-N-(3-pyridyl)-2,3,5,6-tetrahydro-1H-cyclobuta[f]indole-1-carboxamide, 6-cyano-6-(phenylsulphanyl)-N-(3-pyridyl)-2,3,5,6-tetrahydro-1H-cyclobuta[f]indole-1-carboxamide, 6-cyano-6-cyclohexyl-N-(3-pyridyl)-2,3,5,6-tetrahydro-1H-cyclobuta[f]indole-1-carboxamide, 6-cyclohexyl-N-(3-pyridyl)-2,3,5,6-tetrahydro-1H-cyclobuta[f]indole-1-carboxamide, 6-cyano-N-{6-[(2-methyl-3-pyridyl)oxy]-3-pyridyl}-6-(phenylsulphanyl)-2,3,5,6-tetrahydro-1H-cyclobuta[f]indole-1-carboxamide.

The isomers of the preferred compounds, and also the addition salts with a pharmaceutically acceptable acid or base of the preferred compounds, form an integral part of the invention.

The invention relates also to a process for the preparation of the compounds of formula (I), which is characterised in that there is used as starting material a compound of formula (II):

wherein $R'_1$ represents a group selected from hydrogen, cyano, hydroxymethylene, carboxy and linear or branched $(C_1–C_6)$alkoxycarbonyl, which compound of formula (II) is reacted, under the conditions of reductive amination, with a compound of formula (III):

wherein A represents a linear or branched $(C_1–C_6)$alkyl group, to yield the compounds of formula (IV):

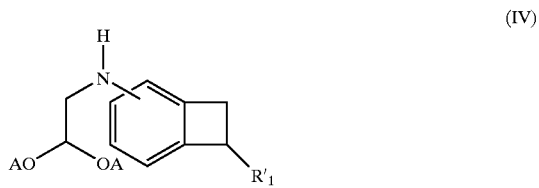

wherein A and $R'_1$ are as defined hereinbefore, which compounds of formula (IV) are treated with a compound of formula (V):

wherein E represents a linear or branched $(C_1–C_4)$alkyl group, phenyl or p-toluyl, to yield the compounds of formula (VI):

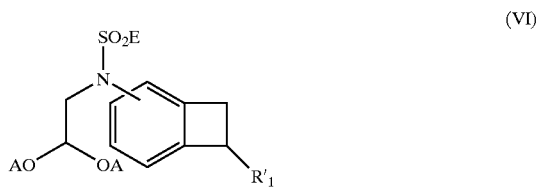

wherein A, E and $R'_1$ are as defined hereinbefore, which compounds of formula (VI) are cyclised under acid conditions to yield the compounds of formula (VII):

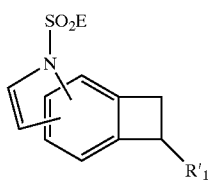

(VII)

wherein E and R'$_1$ are as defined hereinbefore, which compounds of formula (VII) are treated either with an alkali metal hydroxide in an alcoholic solvent or with sodium in liquid ammonia to yield the compounds of formula (VIII):

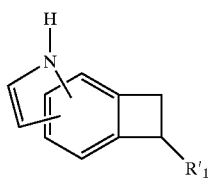

(VIII)

wherein R'$_1$ is as defined hereinbefore, which compounds of formula (VIII) are then reduced, in accordance with the conventional conditions of organic synthesis, to yield the compounds of formula (IX)

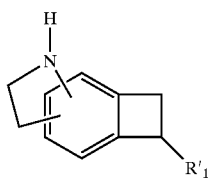

(IX)

wherein R'$_1$ is as defined hereinbefore, which compounds of formula (IX) are treated with an isocyanate of formula (X):

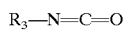

(X)

wherein R$_3$ is as defined for formula (I), to yield the compounds of formula (I/a), a particular case of the compounds of formula (I):

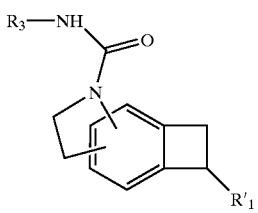

(I/a)

wherein R'$_1$ and R$_3$ are as defined hereinbefore, or which compounds of formula (IX), in the case where R'$_1$ represents a cyano group, are treated:

either with a ketone of formula (XI):

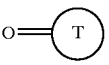

(XI)

wherein T is as defined for formula (I), to yield the compounds of formula (XII):

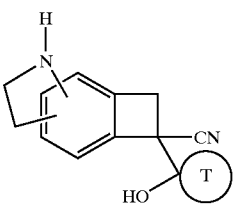

(XII)

wherein T is as defined hereinbefore, which compounds of formula (XII) are then:
either treated with an isocyanate of formula (X) as described hereinbefore to yield the compounds of formula (I/b), a particular case of the compounds of formula (I),

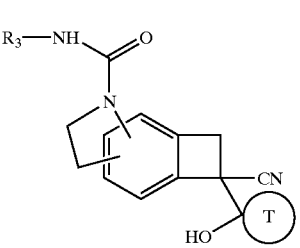

(I/b)

wherein T and R$_3$ are as defined hereinbefore, or, after protection of the amine of the indoline group, reduced according to the conventional methods of organic synthesis to yield the compounds of formula (XIII):

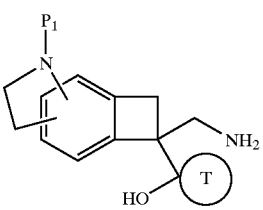

(XIII)

wherein T is as defined hereinbefore and P$_1$ is a conventional protecting group, the primary amine function of which compounds of formula (XIII) is then substituted and converted into the secondary and then tertiary amine function, using conventional methods of organic chemistry, to yield the compounds of formula (XIV):

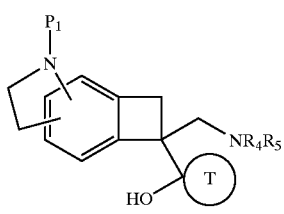

(XIV)

wherein $R_4$ and $R_5$ are as defined for formula (I) and T and $P_1$ are as defined hereinbefore, which compounds of formula (XIV), after deprotection of the nitrogen atom of the indoline nucleus, are treated with a compound of formula (X) as described hereinbefore to yield the compounds of formula (I/c), a particular case of the compounds of formula (I):

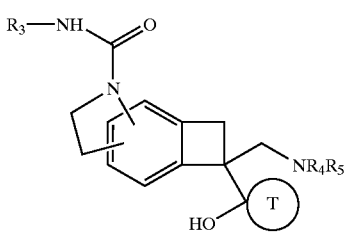

(I/c)

wherein T, $R_4$, $R_5$ and $R_3$ are as defined hereinbefore,
or with a strong base or an alkali metal alcoholate, in the presence of a compound of formula (XV):

$$W_1—X \quad (XV)$$

wherein $W_1$ represents a linear or branched $(C_1-C_6)$alkyl group, an aryl-$(C_1-C_6)$alkyl group in which the alkyl moiety may be linear or branched, a cycloalkyl group, or a cycloalkyl-$(C_1-C_6)$alkyl group in which the alkyl moiety may be linear or branched, and X represents a leaving group, such as a halogen atom or a trifluoromethylsulphonate, mesylate or tosylate group, to yield the compounds of formula (XVI):

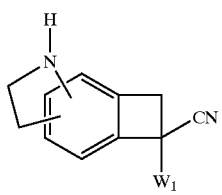

(XVI)

wherein $W_1$ is as defined hereinbefore, which compounds of formula (XVI) are:
either treated with a compound of formula (X) as described hereinbefore to yield the compounds of formula (I/d), a particular case of the compounds of formula (I):

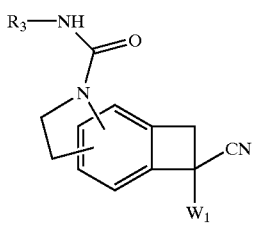

(I/d)

wherein $W_1$ and $R_3$ are as defined hereinbefore,
or, after protection of the nitrogen atom of the indoline nucleus, converted like the compounds of formula (XII) to primary, secondary and then tertiary amine to yield, after deprotection and treatment in the presence of a compound of formula (X) as described hereinbefore, the compounds of formula (I/e), a particular case of the compounds of formula (I):

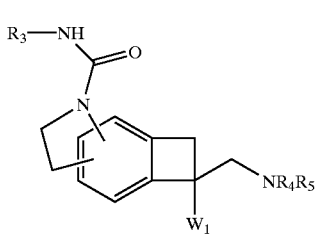

(I/e)

wherein $W_1$, $R_3$, $R_4$ and $R_5$ are as defined hereinbefore,
or with bromine in a chlorine-containing organic solvent to yield the compounds of formula (XVII):

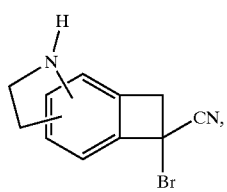

(XVII)

which compounds of formula (XVII) are reacted with a compound of formula (XVIII):

$$W—V_1—H \quad (XVIII)$$

wherein W is as defined for formula (I) and $V_1$ represents an oxygen atom or a sulphur atom,
to yield the compounds of formula (XIX):

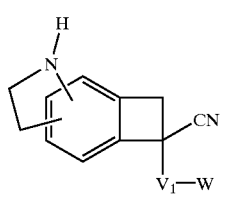

(XIX)

wherein $V_1$ and W are as defined hereinbefore,
which compounds of formula (XIX) are:
either treated with a compound of formula (X) as described hereinbefore to yield the compounds of formula (I/f), a particular case of the compounds of formula (I):

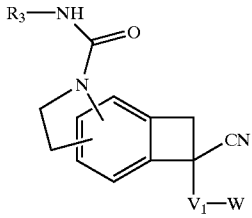
(I/f)

wherein $R_3$, $V_1$ and W are as defined hereinbefore, which compounds of formula (I/f), in the case where $V_1$ represents a sulphur atom, may be subjected to oxidation under conventional conditions of organic synthesis to yield the compounds of formula (I/g), a particular case of the compounds of formula (I):

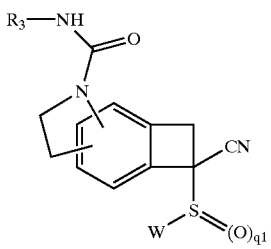
(I/g)

wherein $R_3$ and W are as defined for formula (I) and $q_1$ is an integer of from 1 to 2 inclusive, or protected and then converted, by the same sequence of reactions as the compounds of formula (XII), to primary, secondary and tertiary amine to yield, after deprotection and treatment with a compound of formula (X), as described hereinbefore, the compounds of formula (I/h), a particular case of the compounds of formula (I):

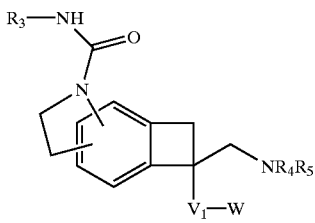
(I/h)

wherein $V_1$, W, $R_3$, $R_4$ and $R_5$ are as defined hereinbefore, which compounds of formula (I/h), in the case where $V_1$ represents a sulphur atom, may be subjected to oxidation under conventional conditions of organic synthesis to yield the compounds of formula (I/i), a particular case of the compounds of formula (I):

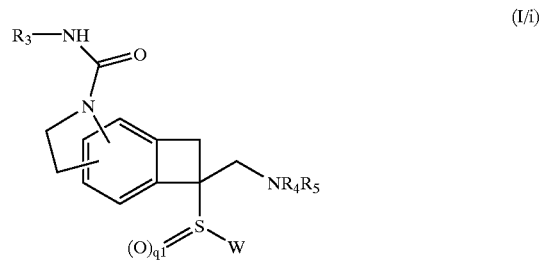
(I/i)

wherein W, $R_3$, $R_4$, $R_5$ and $q_1$ are as defined hereinbefore, or with an alkali metal hydride in dimethylformamide, in the presence of formaldehyde, to yield the compounds of formula (XX):

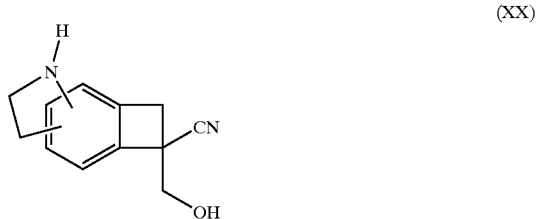
(XX)

which compounds of formula (XX) are:
either treated with a compound of formula (X) as described hereinbefore to yield the compounds of formula (I/j), a particular case of the compounds of formula (I):

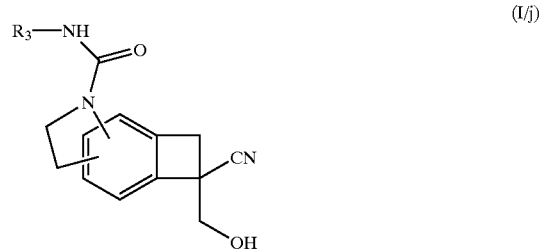
(I/j)

wherein $R_3$ is as defined for formula (I),
or protected at the nitrogen atom of the indoline nucleus, then treated according to Mitsunobu reaction conditions with a compound of formula (XXI):

W—OH  (XXI)

wherein W is as defined for formula (I),
to yield, after deprotection of the nitrogen atom of the indoline nucleus, the compounds of formula (XXII):

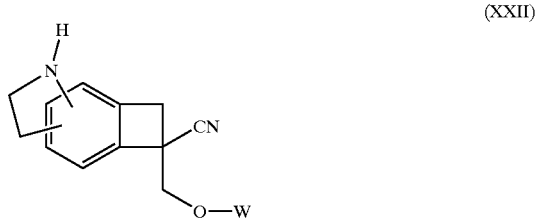
(XXII)

wherein W is as defined hereinbefore, which compounds of formula (XXII) are:
either treated with a compound of formula (X) as described hereinbefore to yield the compounds of formula (I/k), a particular case of the compounds of formula (I):

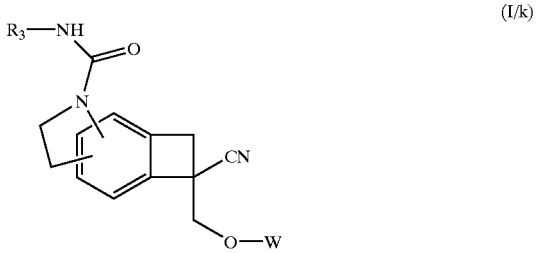

(I/k)

wherein $R_3$ and W are as defined hereinbefore,
or protected and then converted, by the same reaction sequence as the compounds of formula (XII), to primary, secondary and tertiary amine to yield, after deprotection and treatment with a compound of formula (X), as described hereinbefore, the compounds of formula (I/l), a particular case of the compounds of formula (I):

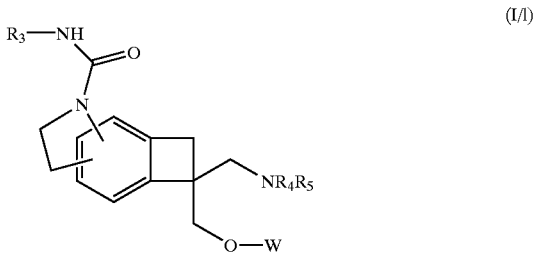

(I/l)

wherein $R_3$, $R_4$, $R_5$ and W are as defined hereinbefore,
the compounds (I/a) to (I/l) constituting the totality of the compounds of the invention, which compounds are purified, if necessary, according to a conventional purification technique, may be separated, if desired, into their different isomers according to a conventional separation technique, and are converted, if desired, into addition salts with a pharmaceutically acceptable acid or base.

The compounds of formulae (II), (III), (V), (X), (XI), (XV), (XVIII) and (XXI) are either known products, or products obtained from known substances according to conventional procedures in organic chemistry.

In view of their pharmacological properties, the compounds of the present invention are useful as medicaments in the treatment of anxiety, panic attacks, obsessive-compulsive disorders, phobias, impulsive disorders, drug abuse, cognitive disorders, psychoses, depression, and mood disorders.

The present invention relates also to pharmaceutical compositions comprising as active ingredient at least one compound of formula (I), an optical isomer thereof or an addition salt thereof with a pharmaceutically acceptable acid or base, alone or in combination with one or more pharmaceutically acceptable, inert, non-toxic excipients or carriers.

Among the pharmaceutical compositions according to the invention there may be mentioned more especially those which are suitable for oral, parenteral (intravenous, intramuscular or subcutaneous) per- or trans-cutaneous, nasal, rectal, perlingual, ocular or respiratory administration, and especially tablets or dragees, sublingual tablets, soft gelatin capsules, hard gelatin capsules, suppositories, creams, ointments, dermal gels, injectable or drinkable preparations, aerosols, eye or nose drops, etc.

The useful dosage varies in accordance with the age and weight of the patient, the administration route, the nature and severity of the disorder and the administration of possible associated treatments and ranges from 0.5 mg to 25 mg in one or more administrations per day.

The following Examples illustrate the invention but do not limit it in any way. The starting materials used are known products or products prepared according to known procedures. The various Preparations result in synthesis intermediates for use in the preparation of the compounds of the invention.

The structures of the compounds described in the Examples were determined according to customary spectrophotometric techniques (infrared, nuclear magnetic resonance, mass spectrometry, . . . ).

The melting points were determined using either a Kofler hot plate (K.), or a hot plate under microscope (M.K.). Where the compound exists in salt form, the melting point given corresponds to that of the product in salt form.

For information only, the numbering used for the tricyclic systems is as follows:

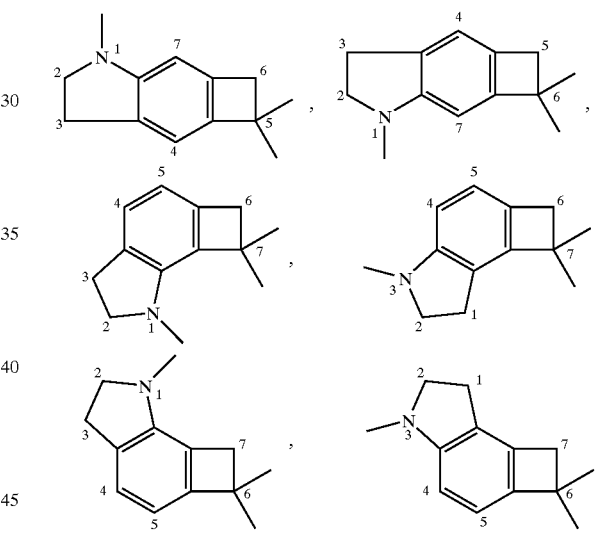

PREPARATION 1

2,3,5,6-Tetrahydro-1H-cyclobuta[f]indo-6-carbonitrile

Step 1: 5-[(2,2-Dimethoxyethyl)amino]benzocyclobutane-1-carbonitrile

To a suspension of 13.5 g of 5-aminobenzocyclobutane-1-carbonitrile in 400 ml of 1,2-dichloroethane there are added rapidly dropwise 26.5 ml of a 45% solution of 2,2-dimethoxyacetaldehyde in tert-butyl methyl ether, followed by 16 ml of acetic acid and then, in portions, 39.7 g of sodium triacetoxyborohydride. After increasing the temperature to 29° C., the reaction mixture is brought to ambient temperature, stirred for 1 hour 15 minutes and then hydrolysed by pouring the mixture into 500 ml of a saturated aqueous solution of $NaHCO_3$. The organic phase is removed, washed with water, and concentrated under reduced pressure to yield the desired product.

Step 2: 5-[N-(2,2-Dimethoxethyl)-N-(methylsulphonyl)amino]benzocyclobutane-1-carbonitrile 10.8 ml of mesyl chloride are added in the course of 20 minutes to a solution, cooled to 0° C., of 21.6 g of the product obtained in Step 1, 58 ml of pyridine and 225 ml of dichloromethane. After stirring for 40 minutes at 0° C., and then for 20 hours at ambient temperature, the reaction mixture is poured into 40 ml of a saturated aqueous solution of NaHCO$_3$. After decanting and extracting twice with 150 ml of dichloromethane each time, the combined organic phases are washed with 1N hydrochloric acid, dried, and then concentrated under reduced pressure to yield the expected product.

Step 3: 1-(Methylsulphonyl)-5,6-dihydro-4H-cyclobuta[f]indole-6-carbonitrile

In the course of 1 hour 15 minutes, a solution of 10.9 ml of titanium chloride in 450 ml of toluene and a solution of 27.9 g of the product obtained in Step 2 in 450 ml of toluene are simultaneously poured into 2 liters of toluene at reflux. When the addition is complete, the temperature is allowed to drop to 40° C., and the whole is then poured into 1.8 liters of a saturated aqueous solution of NaHCO$_3$. After decanting, the aqueous phase is extracted with toluene, and the organic phases are combined, washed, dried and concentrated. The residue is purified by chromatography on silica gel (dichloromethane/cyclohexane:75/25) allowing the expected product and its regioisomer to be isolated.

Melting point: 142–144° C. (M.K.).

Step 4: 5,6-Dihydro-1H-cyclobuta[f]indole-6-carbonitrile 2.6 g of the product obtained in Step 3 are introduced into a solution of 7.7 g of potassium hydroxide in 190 ml of methanol. After 12 hours at reflux, the methanol is evaporated off and the residue is taken up in ether. After washing, the organic phase is dried and concentrated to yield the expected product.

Melting point: 126–128° C. (M.K).

Step 5: 2,3,5,6-tetrahydro-1H-cyclobuta[f]indole-6-carbonitrile 3.43 g of the product obtained in Step 4 are dissolved in 55 ml of acetic acid. In the course of 5 minutes, 3.84 g of sodium cyanoborohydride are added in portions to the reaction mixture, which has been cooled to 13° C. After returning to ambient temperature, stirring is carried out for 2 hours, and then the reaction mixture is cooled to 0° C. and the pH is adjusted to 11 by the addition of a solution of sodium hydroxide (45 g in 250 ml of water). The milky solution obtained is extracted with ether. The organic phases are washed, dried and concentrated to yield the expected product.

Melting point: 85–87° C. (M.K.).

PREPARATION 2

2,3,6,7-Tetrahydro-1H-cyclobuta[e]indole-7-carbonitrile

Step 1: 6,7-Dihydro-3-H-cyclobuta[e]indole-7-carbonitrile

The product is obtained in accordance with the procedure in Step 4 of Preparation 1, using as substrate the regioisomer obtained in Step 3 of Preparation 1.

Step 2: 2,3,6,7-Tetrahydro-1H-cyclobuta[f]indole-7-carbonitrite

Starting from the compound obtained in Step 1, the product is obtained in accordance with the procedure in Step 5 of Preparation 1.

PREPARATION 3

2,3,5,6-Tetrahydro-1H-cyclobuta[f]indole

Step 1: 4-[(2,2-Dimethoxyethyl)amino]benzocyclobutane

A solution of 1 g of the product obtained in Step 1 of Preparation 1 in 20 ml of tetrahydrofuran and 0.22 ml of anhydrous ethanol is added, at −70° C., to 40 ml of liquid ammonia. 322 mg of sodium are then added in portions and stirring is carried out for 20 minutes at −70° C. The reaction is terminated by the addition of 1.72 g of NH$_4$Cl, and all of the ammonia is evaporated off. The reaction mixture is taken up in a saturated NH$_4$Cl solution and then extracted with ether. The organic phase is subsequently dried and concentrated to yield the expected product.

Step 2: 2,3,5,6-Tetrahydro-1H-cyclobuta[f]indole

The product is obtained in accordance with the procedure in Preparation 1, Steps 2 to 5.

Melting point: 68–70° C.

PREPARATION 4

2,3,5,6-Tetrahydro-1H-cyclobuta[f]indol-6-ylmethanol

Step 1: Methyl 5-Amino-1-benzocyclobutanecarboxylate 9.74 g of methyl 5-nitro-1-benzocyclobutanecarboxylate are hydrogenated for 6 hours 30 minutes, at ambient temperature and atmospheric pressure, in the presence of 10% Pd/C. After filtration and concentration under reduced pressure, the expected product is isolated.

Step 2: Methyl 5-[(2,2-Dimethoxyethyl)amino]-1-benzocyclobutanecarboxylate

Starting from the compound of the above Step, the product is obtained in accordance with the procedure in Step 1 of Preparation 1.

Step 3: Methyl 5[N-(2,2-Dimethoxyethyl)-N-(methylsulphonyl)amino]-1-benzocyclobutanecarboxylate Starting from the compound of the above Step, the product is obtained in accordance with the procedure in Step 2 of Preparation 1.

Step 4: Methyl 1-(Methylsulphonyl)-5,6-dihydro-1H-cyclobuta[f]indole-6-carboxylate Starting from the compound of the above Step, the product is obtained in accordance with the procedure in Step 3 of Preparation 1.

Step 5: [1-(Methylsulphonyl)-5,6-dihydro-1H-cyclobuta[f]indol-6-yl]methanol

A solution of 1.6 g of the product obtained in Step 4 in 20 ml of tetrahydrofuran is added dropwise to a suspension of 0.42 g of lithium aluminium hydride in 7 ml of tetrahydrofuran maintained at 0° C. After 20 minutes, the reaction mixture is hydrolysed with 0.3 ml of water, 0.23 ml of 20% sodium hydroxide solution and then 1.05 ml of water. After removal of the salts by filtration, the filtrate is concentrated under reduced pressure to yield the expected product.

Step 6: 5,6-Dihydro-1H-cyclobuta[f]indol-6-ylmethanol

Starting from the compound of the above Step, the product is obtained in accordance with the procedure in Step 4 of Preparation 1.

Step 7:2,3,5,6-Tetrahydro-1H-cyclobuta[f]indol-6-ylmethanol

Starting from the compound of the above Step, the product is obtained in accordance with the procedure in Step 5 of Preparation 1. The compound is isolated by chromatography on silica gel (dichloromethane/ethanol:97/3).

PREPARATION 5

2,3,6,7-Tetrahydro-1H-cyclobuta[g]indol-7-ylmethanol

Step 1: 6-Acetyl-1-benzocyclobutanecarbonitrile

A solution composed of 55.94 g of 6-trifluoroacetyl-1-benzocyclobutanecarbonitrile in 600 ml of pyridine is purged with nitrogen for 15 minutes; 30.5 ml of triethylamine, 117.44 ml of butyl vinyl ether, 2.25 g of 1,3-bis-(diphenylphosphino)propane and 1.02 g of palladium acetate are added and the reaction mixture is heated at reflux for 2 hours. 400 ml of 1N hydrochloric acid are then added dropwise in the course of 1 hour and, after stirring for 3 hours at ambient temperature, the reaction mixture is extracted with ether. The organic phases are washed, dried and concentrated to yield a residue, which is purified by chromatography on silica gel (dichloromethane: 100%) allowing the expected product to be isolated.

Melting point: 55–59° C.

Step 2: 6-Hydroxyiminoethyl-1-benzocyclobutanecarbonitrile 10.07 g of the product of Step 1 and 6.13 g of hydroxylamine hydrochloride in 200 ml of pyridine are stirred at ambient temperature for 19 hours. After removal of the pyridine by evaporation, the yellow oil obtained is taken up in dichloromethane and water. The organic phase is removed, dried and concentrated, allowing the expected product to be isolated.

Melting point: 108–110° C.

Step 3: N-(1-Cyanobenzocyclobutan-6-yl)acetamide 9.96 g of $PCl_5$ are added in four lots to a solution, cooled to 0° C., of 8.9 g of the product obtained in Step 2 in 160 ml of ether. After stirring for 2 hours at 0° C., the reaction mixture is brought to ambient temperature for 12 hours and then poured into a water/ice mixture and stirred for 20 minutes. After decanting and extracting with ether, the combined organic phases are dried and then concentrated under reduced pressure to yield the expected product.

Melting point: <50° C.

Step 4: Ethyl 6-Amino-1-benzocyclobutanecarboxylate

A stream of gaseous HCl is introduced until a solution of 5.04 g of the product obtained in Step 3 in 400 ml of anhydrous ethanol at 0° C. is saturated. The reaction mixture is then heated at reflux for 18 hours. After concentrating the solvent, the residue is taken up in iced water, rendered basic with a sodium carbonate solution and extracted with dichloromethane. The organic phase is removed, dried and concentrated to yield the expected product.

Step 5: 2,3,6,7-Tetrahydro-1H-cyclobuta[g]indol-7-ylmethanol

Starting from the compound of the above Step, the product is obtained according to the procedures in Steps 2 to 7 of Preparation 4.

PREPARATION 6

2,3,5,6-Tetrahydro-1H-cyclobuta[f]indole-5-carbonitrile

The product is obtained in accordance with the procedure in Preparation 1, Steps 1 to 5, using as substrate in Step 1 4-amino-1-benzocyclobutanecarbonitrile.

Melting point: 103–107° C.

PREPARATION 7

2,3,5,6-Tetrahydro-1H-cyclobuta[f]indol-5-ylmethanol

The product is obtained in accordance with the procedure in Preparation 4, Steps 1 to 7, using as substrate in Step 1 ethyl 4-nitro-1-benzocyclobutanecarboxylate.

PREPARATION 8

Nicotinoyl Azide

There are added to a suspension of 12.3 g of nicotinic acid in 100 ml of dimethylformamide 14.2 ml of triethylamine and then, after cooling to 0° C., 22 ml of diphenylphosphoryl azide in 50 ml of dimethylformamide. After stirring for 2 hours, the reaction mixture is poured onto ice. After extraction with ether, the organic phase is washed with a $NaHCO_3$ solution, dried, and then concentrated to yield 9.68 g of the expected product.

PREPARATION 9

Phenyl 6-[(2-Methyl-3-pyridyl)oxy]-3-pyridylcarbamate

Step 1: 6-[(2-Methyl-3-pyridyl)oxy]-3-pyridylamine

A solution of 14.35 g of tin chloride in 30 ml of concentrated hydrochloric acid is added to a mixture of 5 g of 2-(2-methylpyrid-3-yloxy)-5-nitropyridine and the whole is heated at reflux for 1 hour. The reaction mixture is cooled and adjusted to basic pH by the addition of concentrated sodium hydroxide solution. After the removal of a precipitate by filtration, the aqueous phase is extracted with ethyl acetate. After conventional working up, the expected product is isolated in the form of a violet powder.

Melting point: 95–100° C. (M.K.).

Step 2: Phenyl 6-[(2-Methyl-3-pyridyl)oxy]-3-pyridylcarbamate 3 ml of methyl chloroformate are added dropwise to a solution, maintained at −20° C., of 4.5 g of the product obtained in Step 1, 3.3 ml of triethylamine and 180 ml of dichloromethane. After returning to ambient temperature, the reaction mixture is washed with sodium hydrogen carbonate, dried and concentrated under reduced pressure. Chromatography on silica gel of the residue (dichloromethane/ethanol/$NH_4OH$:98/2/0.29) allows the expected product to be isolated.

EXAMPLE 1

N-(3-Pyridyl)-2,3,5,6-tetrahydro-1H-cyclobuta[f]indole-1-carboxamide 7.4 g of the compound of Preparation 8 in 40 ml of toluene are heated at reflux for 2 hours 30 minutes, then cooled to ambient temperature. 0.99 g of the product of Preparation 3 dissolved in 50 ml of dichloromethane are then added dropwise. After stirring for 18 hours, the reaction mixture is filtered and the filtrate is concentrated under reduced pressure. Chromatography on silica gel (dichloromethane/ethanol:95/5) allows isolation of the expected product, which is then recrystallised from ethanol.

Melting point: 178–180° C. (M.K.).

EXAMPLE 2

6-(Hydroxymethyl)-N-(3-pyridyl)-2,3,5,6-tetrahydro-1H-cyclobuta[f]indole-1-carboxamide The product is obtained in accordance with the procedure in Example 1, using as substrate the compound of Preparation 4.

Melting point: 195–200° C. (M.K.).

EXAMPLE 3

6-Cyano-N-(3-pyridyl)-2,3,5,6-tetrahydro-1H-cyclobuta[f]indole-1-carboxamide

The product is obtained in accordance with the procedure in Example 1, using as substrate the compound of Preparation 1.

Melting point: 203–207° C. (M.K).

EXAMPLE 4

5-Cyano-N-(3-pyridyl)-2,3,5,6-tetrahydro-1H-cyclobuta[f]indole-1-carboxamide The product is obtained in accordance with the procedure in Example 1, using as substrate the compound of Preparation 6.

Melting point: 209–211° C. (M.K.).

EXAMPLE 5

5-(Hydroxymethyl)-N-(3-pyridyl)-2,3,5,6-tetrahydro-1H-cyclobuta[f]indole-1-carboxamide The product is obtained in accordance with the procedure in Example 1, using as substrate the compound of Preparation 7.

Melting point: 167–173° C. (M.K.).

EXAMPLE 6

7-Cyano-N-(3-pyridyl)-1,2,6,7-tetrahydro-3H-cyclobuta[e]indole-3-carboxamide The product is obtained in accordance with the procedure in Example 1, using as substrate the compound of Preparation 2.

Melting point: 203–205° C. (M.K.).

EXAMPLE 7

7-(Hydroxymethyl)-N-(3-pyridyl)-2,3,6,7-tetrahydro-1H-cyclobuta[g]indole-1-carboxamide The product is obtained in accordance with the procedure in Example 1, using as substrate the compound of Preparation 5.

Melting point: 216–220° C. (M.K).

EXAMPLE 8

6-[(Dimethylamino)methyl]-6-(1-hydroxycyclohexyl)-N-(3-pyridyl)-2,3,5,6-tetrahydro-1H-cyclobuta[f]indole-1-carboxamide Step 1: 6-(1-Hydroxycyclohexyl)-2,3,5,6-tetrahydro-1H-cylobuta[f]indole-6-carbonitrile 4.1 g of the product obtained in Preparation 1 are dissolved in 215 ml of tetrahydrofuran. The reaction mixture is cooled to –80° C. and 19.25 ml of a 2.5M solution of n-butyllithium in hexane are added using a push-syringe. When the addition is complete, stirring is carried out for 20 minutes and then 6.2 ml of cyclohexanone are poured in in the course of 3 minutes. After contact at –80° C. for two hours, the whole is allowed to return to ambient temperature, and 23 ml of a saturated aqueous solution of ammonium chloride and also 135 ml of water are added. After decanting, the organic phase is washed with a saturated sodium chloride solution, dried and concentrated. The residue obtained is solidified with isopropyl ether and filtered to obtain the desired product, and the filtrate is purified by chromatography on silica gel (CH$_2$Cl$_2$/AcOEt: 90/10) in order to isolate an additional amount of the expected product.

Melting point: 168–170° C.

Step 2: 6-(1-Hydroxycyclohexyl)-1-(methylsulphonyl)-2,3,5,6-tetrahydro-1H-cyclobuta[f]indole-6-carbonitrile 4 g of the product obtained in Step 1 are reacted under the conditions in Step 2 of Preparation 1.

Step 3: 1-[6-(Aminomethyl)-1-(methylsulphonyl)-2,3,5,6-tetrahydro-1H-cyclobuta[f]indol-6-yl]cyclohexanol 5.5 g of the product obtained in Step 2 are dissolved in 250 ml of a 3.6N solution of ammoniacal methanol containing 2 mg of Raney nickel. The reaction mixture is hydrogenated for 24 hours at 60° C. under a pressure of 30 bar. After filtration and removal of the solvent by evaporation, the residue is taken up in dichloromethane, washed with water until neutral, dried and concentrated to isolate the expected product.

Step 4: 1-[6-[(Dimethylamino)methyl]-1-(methylsulphonyl)-2,3,5,6-tetrahydro-1H-cyclobuta[f]indol-6-yl]cyclohexanol 5.37 g of the amine obtained in Step 3 are dissolved in 130 ml of acetonitrile. There are introduced into the solution, which has been cooled to 0° C., 2.9 g of sodium cyanoborohydride and 6.9 ml of a 37% formaldehyde solution in water, while maintaining the temperature at 0° C. After 20 hours' reaction at ambient temperature, the mixture is hydrolysed with 210 ml of 1N hydrochloric acid and then stirred for 3 hours. The reaction mixture is washed with 30 ml of ether and then rendered basic using 20% sodium hydroxide solution. The aqueous phase is extracted with dichloromethane. After drying and evaporation, the residue is purified by chromatography on silica gel (CH$_2$Cl$_2$/EtOH:95/5) to yield the expected product.

Melting point: 156–158° C. (M.K.).

Step 5: 1-{6-[(Dimethylamino)methyl]-2,3,5,6-tetrahydro-1H-cylobuta[f]indol-6-yl}cyclohexanol 3.75 g of the product obtained in Step 4 in 100 ml of tetrahydrofuran are added dropwise to 400 ml of liquid ammonia cooled to –50° C. 0.56 g of sodium are added in portions, and stirring is carried out for 15 minutes. The reaction is terminated by the addition of 2.65 g of ammonium chloride. The whole is allowed to return to ambient temperature to evaporate the ammonia, and is then taken up in water and extracted with ether. Drying, evaporation and recrystallisation from acetonitrile are carried out to yield the expected product.

Melting point: 159–161° C. (M.K.).

Step 6: 6-[(Dimethylamino)methyl]-6-(1-hydroxycylohexyl)-N-(3-pyridyl)-2,3,5,6-tetrahydro-1H-cylobuta[f]indole-1-carboxamide The product is obtained in accordance with the procedure in Example 1, using as substrate the product obtained in Step 5.

Melting point: 207–209° C.

EXAMPLE 9

6-Cyan-6-(phenylsulphanyl)-N-(3-pyridyl)-2,3,5,6-tetrahydro-1H-cyclobuta[f]indole-1-carboxamide Step 1: 6-(Phenylsulphanyl)-2,3,5,6-tetrahydro-1H-cylobuta[f]indole-6-carbonitrile 15 ml of a 1.6N solution of n-butyllithium in hexane are added in the course of 30 minutes to a solution, cooled to –70° C., of 2 g of the product of Preparation 1 dissolved in 40 ml of tetrahydrofuran, and then 2.82 g of diphenyl sulphide dissolved in 8 ml of tetrahydrofuran are poured in. The reaction mixture is slowly brought to ambient temperature. After reaction for 2 hours, the mixture is poured into 1.2 liters of a saturated ammonium chloride solution and then extracted with ether. The combined organic phases are purified by acidbase exchange, allowing the expected product to be isolated.

Step 2: 6-Cyano-6-(phenylsulphanyl)-N-(3-pyridyl)-2,3,5, 6-tetrahydro-1H-cyclobuta[f]indole-1-carboxamide 0.43 g of the product obtained in Step 1 are treated with 0.297 g of the compound of Preparation 8 in accordance with the procedure described in Example 1, allowing the expected product to be obtained.

Melting point: 110–113° C. (M.K.).

EXAMPLE 10

6-Cyano-6-cyclohexyl-N-(3-pyridyl)-2,3,5,6-tetrahydro-1H-cyclobuta[f]indole-1-carboxamide Step 1: 6-Cyclohexyl-2,3,5,6-tetrahydro-1H-cyclobuta[f]indole-6-carbonitrile 15 ml of a 1.6N solution of n-butyllithium in hexane are added in the course of 30 minutes to a solution, cooled to −70° C., of 2 g of the product of Preparation 1 dissolved in 20 ml of tetrahydrofuran. After contact for 30 minutes, 2.17 ml of bromocyclohexane are poured in in the course of 25 minutes and the reaction mixture is progressively brought to −20° C. and then poured into a saturated ammonium chloride solution and finally extracted with ether. Purification on silica (dichloromethane/ethyl acetate:95/5) yields the expected product in the form of an oil.

Step 2: 6-Cyano-6-cyclohexyl-N-(3-pyridyl)-2,3,5,6-tetrahydro-1H-cylobuta[f]indole-1-carboxamide 0.33 g of the product obtained in Step 1 are treated with 0.25 g of the compound of Preparation 8 in accordance with the procedure described in Example 1, allowing the expected product to be obtained.

Melting point: 224–227° C.

EXAMPLE 11

6-Cyclohexyl-N-(3-pyridyl)-2,3,5,6-tetrahydro-1H-cyclobuta[f]indole-1-carboxamide Step 1: 6-Cyclohexyl-2,3,5,6-tetrahydro-1H-cyclobuta[f]indole A solution of 0.5 g of the product obtained in Step 1 of Example 10 in 10 ml of anhydrous tetrahydrofuran and 0.11 ml of absolute ethanol are poured into 20 ml of liquid ammonia at a temperature of −78° C., and then 0.15 g of sodium are introduced in portions. After contact for 30 minutes at that temperature, the reaction mixture is treated with 0.83 g of ammonium chloride. After removal of the ammonia by evaporation, the residue is taken up in a saturated solution of ammonium chloride and extracted with ether and the ethereal phases are washed, dried and concentrated to yield the expected product.

Step 2: 6-Cyclohexyl-N-(3-pyridyl)-2,3,5,6-tetrahydro-1H-cyclobuta[f]indole-1-carboxamide 0.43 g of the product obtained in Step 1 are treated with 0.36 g of the compound of Preparation 8 in accordance with the procedure described in Example 1, allowing the expected product to be obtained.

Melting point: 187–190° C. (M.K).

EXAMPLE 12

6-Cyano-N-{6-[(2-methyl-3-pyridyl)oxy]-3-pyridyl}-6-(phenylsulphanyl)-2,3,5,6-tetrahydro-1H-cyclobuta[f]indole1-carboxamide A mixture composed of 0.5 g of the product obtained in Example 9, 0.6 g of the product of Preparation 9, 0.16 ml of triethylamine and 16 ml of dimethylformamide is heated at 100° C. for 1 hour. After removal of the dimethylformamide by evaporation, the residue is taken up in 100 ml of dichloromethane, washed with 10% sodium hydroxide solution, and with water, and then dried and concentrated under reduced pressure to yield the desired product after purification on silica (dichloromethane/ethanol/NH$_4$OH:98/2/0.4) and recrystallisation from acetonitrile.

PHARMACOLOGICAL STUDY OF THE COMPOUNDS OF THE INVENTION

EXAMPLE 13

Vogel Conflict Test

The test is carried out on male Wistar rats (IFFA-CREDO) weighing from 230 to 250 g, which are kept in groups of 4 on sawdust in cages in an animal house, with free access to food and drink, for 5 days before they are used, under the following conditions: temperature (21±1° C.), humidity (60±5%) and a 12 hour diurnal cycle (07:00 to 19:00 hours).

On the Monday following their arrival, the animals are transferred to the experiment room where they stay until Friday, the day of the test. For 4 days, from Monday to Thursday inclusive, the animals have access to drink for only one hour per day (from 09:00 to 10:00 hours).

On the day before the test, the animals are isolated from 15:00 hours in cages, on grills, without either food or drink.

The test is carried out in a transparent plastics cage located in a soundproofed and ventilated enclosure. The cage has a chrome steel floor. The metal tip of the bottle containing the drink enters the cage at a height of 6 cm above the metal floor. The floor and the tip of the bottle are connected by electric cables to an apparatus which records the licks of the animal and controls the administration of electric shocks. The apparatus is so regulated that the animal receives an electric shock (between tip and metal floor) every 20 licks of the tip.

On the day of the test, the animal is given an injection (s.c.) of physiological serum (control) or of the test product 30 minutes before being placed in the test cage. The session begins as soon as the animal has carried out 20 licks and received a first electric shock (duration 0.5 seconds, intensity 0.300 mA). For a period of 3 minutes, the animal receives an electric shock each time it carries out 20 licks.

The results are the numbers of licks and of shocks received by the animal during the 3 minutes of the test.

The numbers of licks and of shocks received by the treated animals are compared with those of the control animals by variance analysis, followed by a Dunnett's test with $p<0.05$. An anxiolytic product increases the number of licks and of shocks received by the animal compared with the controls. For information only, the average number of licks not punished in the animals which have been made thirsty is 674.9±44.5 (N=7) over 3 minutes.

The effectiveness of a product is expressed by the minimum effective dose (MED), that is to say, the lowest dose producing a significant difference compared with the controls. That dose is 2.5 mg/kg s.c. for the product of Example 1.

| Results for the product of Example n° 1 | | |
|---|---|---|
| Doses mg/kg, s.c. | Punished licks (1 shock/20 licks) | N |
| 0 | 142.7 ± 31.9 | 10 |
| 0.63 | 197.5 ± 59.5 | 8 |
| 2.5 | 560.1 ± 67.0* | 8 |
| 10.0 | 499.3 ± 95.3* | 7 |

*p < 0.05

EXAMPLE 14

Marble-burying Test in the Mouse

This test allows evaluation of the capacity of pharmacological agents to inhibit the spontaneous marble-burying behaviour of mice, the inhibition being predictive of anti-depressant and/or anti-impulsive action. Male mice of the NMRI strain (Iffa-Credo, l'Arbresle, France) weighing from 20 to 25 g on the day of the experiment are placed individually in Macrolon boxes (30×18×19 cm) containing 5 cm of sawdust and covered with a perforated plexiglass plate. Twenty four "tiger's eye" glass marbles are evenly distributed on the sawdust at the periphery of the box. At the end of 30 minutes' free exploration, the animals are removed from the box and the number of buried marbles is counted.

By way of example, the MED (minimum effective dose) for the product of Example 1 is 2.5 mg/kg s.c.

EXAMPLE 15

Pharmaceutical Composition: Tablets

Formulation for the preparation of 1000 tablets each comprising 5 mg of active ingredient
compound of Example 1 . . . 5 g
hydroxypropyl methylcellulose . . . 5 g
wheat starch . . . 10 g
lactose . . . 100 g
magnesium stearate . . . 2 g

What is claimed is:
1. A compound selected from those of formula (I):

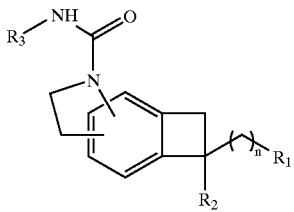

wherein:
n represents integer from 0 to 6,
$R_1$ represents a group selected from hydrogen, hydroxy, cyano, linear or branched ($C_1$–$C_6$)alkoxy, linear or branched ($C_1$–$C_6$)alkoxycarbonyl, and carboxy,
$R_2$ is selected from hydrogen, linear or branched ($C_1$–$C_6$) alkyl, hydroxy, and hydroxymethyl, and
$R_3$ is pyridyl, its isomers, and also addition salts thereof with a pharmaceutically-acceptable acid or base.

2. A compound of claim 1, wherein $R_2$ represents hydrogen, its isomers, and also addition salts thereof with a pharmaceutically-acceptable acid or base.

3. A compound of claim 1, wherein n is 0, $R_1$ represents hydrogen, or cyano, and $R_2$ represents hydrogen, its isomers, and also addition salts thereof with a pharmaceutically-acceptable acid or base.

4. A compound of claim 1, wherein $R_3$ represents pyridyl, its isomers, and also addition salts thereof with a pharmaceutically-acceptable acid or base.

5. A compound of claim 1 that is selected from:
N-(3-pyridyl)-2,3,5,6-tetrahydro-1H-cyclobuta[f]indole-1-carboxamide,
5-cyano-N-(3-pyridyl)-2,3,5,6-tetrahydro-1H-cyclobuta[f]indole-1-carboxamide,
6-cyano-N-(3-pyridyl)-2,3,5,6-tetrahydro-1H-cyclobuta[f]indole-1-carboxamide,
6-(hydroxymethyl)-N-(3-pyridyl)-2,3,5,6-tetrahydro-1H-cyclobuta[f]indole-1-carboxamide,
5-(hydroxymethyl)-N-(3-pyridyl)-2,3,5,6-tetrahydro-1H-cyclobuta[f]indole-1-carboxamide,
7-cyano-N-(3-pyridyl)-1,2,6,7-tetrahydro-3H-cyclobuta[e]indole-3-carboxamide, and
7-(hydroxymethyl)-N-(3-pyridyl)-2,3,6,7-tetrahydro-1H-cyclobuta[g]indole-1-carboxamide,
its isomers, and also addition salts thereof with a pharmaceutically acceptable acid or base.

6. A method for treating a living animal body afflicted with a condition selected from anxious conditions, impulsive disorders, psychoses, depression and mood disorders, comprising the step of administering to the living body an amount of a compound of claim 1 which is effective for alleviation of said conditions.

7. A pharmaceutical composition useful in treating a living animal body afflicted with a condition selected from anxious conditions, impulsive disorders, psychoses, depression and mood disorders comprising as active principle an effective amount of a compound as claimed in claim 1, together with one or more pharmaceutically-acceptable excipients or vehicles.

* * * * *